United States Patent [19]

Bolliger et al.

[11] Patent Number: 4,913,653
[45] Date of Patent: Apr. 3, 1990

[54] AXIS INDICATOR FOR ORTHODOTIC BRACKET

[75] Inventors: Diane K. Bolliger, San Diego; Howard Graham, La Mesa, both of Calif.

[73] Assignee: Johnson & Johnson Consumer Products, Inc., New Brunswick, N.J.

[21] Appl. No.: 325,744

[22] Filed: Mar. 20, 1989

[51] Int. Cl.⁴ ............................................. A61C 7/00
[52] U.S. Cl. ........................................ 433/3; 433/14
[58] Field of Search ................................ 433/2, 3, 14

[56] References Cited

U.S. PATENT DOCUMENTS 3,521,355  7/1970  Pearlman ................................. 433/3
4,523,908  6/1985  Drisaldi et al. ......................... 433/3

OTHER PUBLICATIONS

Transcend Catalog, pages 5 and 6 Copyright 1987, Unitek Corporation.
TP Orthodontics, Inc. Catalog Cover.

Primary Examiner—Robert Peshock
Attorney, Agent, or Firm—Paul A. Coletti

[57] ABSTRACT

An axis indicator contains a long rectangular tube placed within the saddle of a dental bracket. The indicator contains a projection which is parallel to the archwire slot in the dental bracket and can be aligned parallel to the occlusal plane of the patient. Thus, use of the axis indicator insures proper placement of the dental bracket on the teeth.

10 Claims, 1 Drawing Sheet

AXIS INDICATOR FOR ORTHODOTIC BRACKET

FIELD OF THE INVENTION

Generally, this invention relates to indicators for orthodontic brackets. Specifically, this invention relates to axis indicators for orthodontic brackets to insure proper placement in the mouth. Most specifically, this invention relates to axis indicators for orthodontic sapphire brackets for proper placement along the crown long axis of the tooth.

BACKGROUND OF THE INVENTION

In the past twenty years, remarkable advances have taken place in the orthodontic field, specifically in the nature of orthodontic brackets. These orthodontic brackets used for straightening teeth have become stronger, smaller, and even less easy to see in the mouth. Specifically, many orthodontic brackets are now made using crystalline or polycrystalline formulas. One such crystalline bracket is the Starfire TM bracket marketed by "A"-Company of San Diego, Calif. Except for the archwire placed within these brackets, it is virtually impossible to detect their placement on the teeth.

A problem encountered during placement of these brackets is proper alignment of the archwire slots along the occlusal plane of the mouth while ensuring that the ridge between tie wings in the brackets is aligned with the crown long axis of the tooth. One previous solution has been to emplace colored plastic between the tie wing ridges and using such plastic to align the bracket with the crown long axis of the tooth. Generally, these colored plastic pieces have been bulky and obtrusive during the emplacement of the bracket on the tooth. This is, generally these brackets have been hindered by the plastic axis indicators when emplaced within the mouth. The axis indicators are so large that they fit around and even over the bracket, and it becomes difficult to tell whether the bracket itself is properly emplaced within the mouth, simply because of the plastic axis indicator.

It is therefore an object of the invention to provide an axis indicator so that the bracket can be aligned with the crown long axis of the tooth.

It is a further object of the present invention to provide an axis indicator wherein the bracket is easily evident, and accessible to the orthodontist during emplacement in the mouth.

It is still a further object of the present invention to provide an axis indicator that conforms to the size of the dental bracket without hiding the dental bracket in the mouth.

It is yet another object of the invention to provide an axis indicator which allows the orthodontist to adjust the dental bracket in the mouth while maintaining the axis indicator on the bracket until the bracket is properly placed in its desired position on the tooth.

It is still another object of the present invention to provide an axis indicator which allows the orthodontist to discern the distal-gingival tie wing of the dental bracket for proper placement on the correct tooth in the mouth.

Finally, it is an object of the present invention to provide an axis indicator which will not be removed from the dental bracket during shipping or during emplacement within the mouth, until the desired placement is made.

SUMMARY OF THE INVENTION

These and other objects of the present invention are accomplished in the present axis indicator which includes a generally rectangular tube conforming to the size of the ridge or saddle between the tie wings on a dental bracket. This generally rectangular tube will contain a pair of detents which create a pressure or interference fit within the tie wing ridges during shipping and even during emplacement of the bracket within the mouth. Extending from this rectangular tube is a flag-like projection which skirts one outer edge of the dental bracket to indicate the distal-gingival tie wing parallel to the archwire slot in the bracket. This projection is, of course, also generally perpendicular to the saddle or ridge of the bracket. In addition, the axis indicator of the present invention contains a slot aligned with the archwire slot of the dental bracket in order to allow use of a dental positioning tool during emplacement of the bracket.

In accordance with the method of the present invention, the axis indicator is made of a color to stand apart from the dental bracket and the teeth so that the axis indicator can be aligned with the crown long axis of the tooth. The bracket is emplaced on the tooth and the archwire strung through the bracket, properly positioned parallel to the occlusal plane. These and other objects of the present invention can be best appreciated in conjunction with the following drawings and detailed description of the invention in which:

DETAILED DESCRIPTION OF THE DRAWINGS

DETAILED DESCRIPTION OF THE INVENTION

Figure 1:
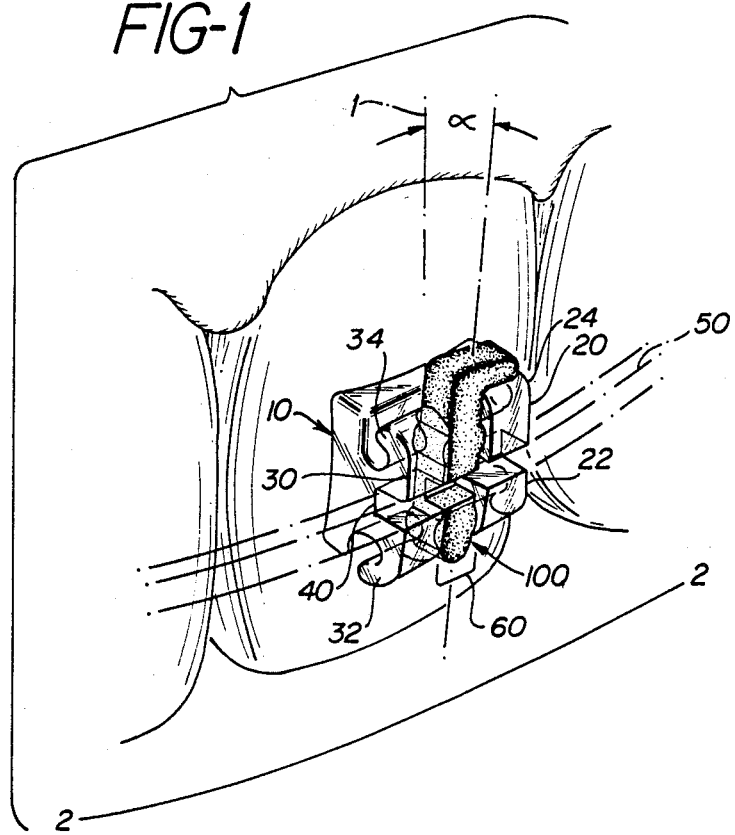
FIG. 1 is a perspective view of a dental bracket containing an axis indicator conforming to a preferred embodiment of the present invention.
Figure 2:
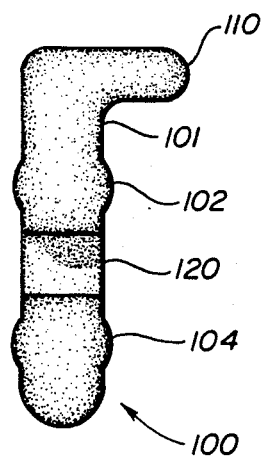
FIG. 2 is a plan view of a preferred embodiment of the present invention.
Figure 3:
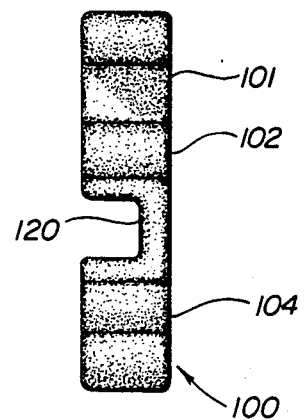
FIG. 3 is an elevation view of a preferred embodiment of the present invention.

In general, dental bracket 10 will contain a distal tie wing 20 and a mesial tie wing 30 separated by archwire slot 40. Archwire 50 is strung through the archwire slot 40 to exert control on the movement of the tooth. In general, it is desirable to have the archwire 50 placed so that it is parallel to the occlusal plane 2 of the mouth. This will insure the steady adjustment of teeth in order to align them with the occlusal plane.

In general, the distal tie wing 20 contains an occlusal edge or tip 22 and a gingival edge or tip 24. Likewise, the mesial tie wing 30 contains an occlusal edge or tip 32 and a gingival edge or tip 34. Both the distal tie wing 20 and the mesial tie wing 30 are separated by a saddle or ridge 60. Most dental brackets are made so that ridge 60 will be aligned with the crown long axis 1 of the tooth. In addition, it becomes necessary for proper placement of the bracket 10 for archwire 50 to be aligned with the occlusal plane 2 of the mouth.

For two important reasons, with clear brackets, such as crystalline and polycrystalline brackets it will be more difficult to determine the proper orientation of the bracket. First, these brackets, as with all conventional modern brackets, may be quite small. They are smaller than even the tooth on which they are to be placed. Second, the brackets are nearly transparent. The bracket will not contrast with the tooth, as is the case with metallic brackets.

The problems with managing small crystalline and polycrystalline dental brackets are resolved by the axis indicator 100 of the present invention. This axis indicator 100 contains a long tube 101, generally rectangular in shape, or any configuration which fits snugly within the saddle 60 of the dental bracket. The axis indicator tube 101 contains detents 102, 104 which create a press or interference fit between the saddle 60 and the indicator 100.

The axis indicator 100 also contains a projection 110 which helps align the dental bracket 10. The projection 110 will be generally parallel to the archwire slot 40 of the dental bracket 10. Of course, the projection 110 as configured in the present invention will be generally perpendicular to the saddle or ridge 60 of the dental bracket 10. Because projection 110 will also contrast with the clear dental bracket 10, the orthodontist can use projection 110 to insure that the parallel pair of lines formed by projection 110 and archwire slot 40 are also properly parallel with the occlusal plane 2. In addition, the projection 110 will provide proper direction in determining the distal and gingival direction of the bracket for bracket orientation. With the bracket 10 properly placed on the tooth, archwire 50 can also properly be aligned with the occlusal plane.

If the dental bracket is of a rhomboidal shape, tube 101 will also be aligned with the tooth long axis 1. With rectangular brackets, the tube 101 will have a parallel offset to the tooth long axis 1, as seen in FIG. 1. Nonetheless, because the projection 110 is aligned with the occlusal plane so that the archwire slot 40 is in its proper place, it is insured that the entire bracket 10 will be properly placed and bonded onto the tooth.

In addition, the axis indicator 100 of the present invention contains a slot 120 in which a dental positioning device can be placed. This slot 120 is aligned with the archwire slot 40 of the dental bracket 10. Thus, an orthodontist's positioning tool will be used before the archwire 50 is emplaced in the entire dental bracket. Once the dental bracket 10 has been bonded to the teeth, the orthodontist can remove the axis indicator 100 and string archwire 50 through the bracket.

The axis indicator 100 is placed in the bracket 10 in a press or interference fit, to prevent the axis indicator 100 from being removed during shipping. This fit will not be so strong that the orthodontist will have difficulty removing it after proper emplacement of the dental bracket 10. Thus, after use of this axis indicator 100, the dental bracket 10 is properly emplaced, the archwire slot 40 of the dental bracket is also parallel to the occlusal plane 2, insuring that the archwire 50 will remain parallel to the occlusal plane, and the axis indicator 100 has served its function.

While the present invention has been described in connection with a particularly preferred embodiment, it is understood that modifications and changes in the present invention will not effect the actual invention, which is to be interpreted from the appended claims and their equivalents.

What is claimed is:

1. An improved axis indicator for use with a dental bracket having a pair of tie wings separated by a ridge and an archwire slot comprising:
   a insert adapted to fit between the tie wings of said bracket in said bracket ridge, said insert containing a projection extending along one outer edge of said bracket and parallel to said archwire slot, said projection used to orient said bracket parallel to the occlusal plane of the mouth insuring that said tie wings are oriented along the crown long axis of the tooth.

2. The axis indicator of claim 1 wherein said insert contains rounded detents extending from said insert surface, said detents maintaining a press fit between said insert and said tie wings.

3. The axis indicator of claim 1 wherein said insert contains a slot configured to fit within said bracket archwire slot, in order to allow the placement of a dental positioning tool within said slots.

4. For use with a dental bracket having an archwire slot and a pair of tie wings separated by a ridge, an axis indicator generally conforming to said ridge between the tie wings and projecting from the tie wings along one tie wing edge parallel to said archwire slot.

5. The axis indicator of claim 4 wherein said insert contains rounded detents extending from said insert surface, said detents maintaining a press fit between said insert and said tie wings.

6. The axis indicator of claim 5 wherein said insert contains a slot configured to fit within said bracket archwire slot in order to allow the placement of a dental positioning tool within said slots.

7. The axis indicator of claim 6 wherein said projection is angled with said rectangular insert at the same angle between said archwire slot and said tie wing ridge such that when placing said axis indicator along the long axis of said tooth said archwire slot will be placed along the occlusal plane of the mouth.

8. A dental bracket axis indicator comprising a generally rectangular insert having one side fitting between the tie wings of said bracket in an interference fit and a projection from said insert extending generally parallel to said bracket archwire slot, said axis indicator used to align said bracket parallel to said archwire slot and along the crown long axis of the tooth.

9. The axis indicator of claim 8 wherein said insert contains rounded detents extending from said insert surface, said detents maintaining said interference fit between said insert and said tie wings.

10. The axis indicator of claim 8 wherein said insert contains a positioning slot configured to fit within said bracket archwire slot in order to allow the placement of a dental positioning tool within said aligned slots.

* * * * *